United States Patent [19]
Wilk et al.

[11] Patent Number: 5,232,663
[45] Date of Patent: Aug. 3, 1993

[54] TEST CARRIER FOR ANALYTICAL DETERMINATION HAVING A HIGHLY EFFECTIVE FIXING LAYER FOR FLOW-THROUGH BOUND/FREE SEPARATION

[75] Inventors: Hans-Erich Wilk, Einhausen; Erich Schneider; Andreas Marschall, both of Mannheim; Manfred Bleisteiner, Mannheim, all of Fed. Rep. of Germany

[73] Assignee: Boehringer Mannheim GmbH, Mannheim, Fed. Rep. of Germany

[21] Appl. No.: 697,566

[22] Filed: May 9, 1991

[30] Foreign Application Priority Data

May 14, 1990 [DE] Fed. Rep. of Germany ....... 4015378

[51] Int. Cl.⁵ .................... G01N 21/78; G01N 31/22
[52] U.S. Cl. ....................... 422/56; 422/57; 422/58; 436/170; 436/530; 436/531; 436/805; 436/810
[58] Field of Search ................... 422/56–58; 436/805, 530, 531, 810, 170

[56] References Cited

U.S. PATENT DOCUMENTS

| | | | |
|---|---|---|---|
| 4,361,537 | 11/1982 | Deutsch et al. | 422/56 |
| 4,472,498 | 9/1984 | Masuda et al. | 422/57 X |
| 4,613,567 | 9/1986 | Yasoshima et al. | 422/58 X |
| 4,806,311 | 2/1989 | Greenquist | 422/56 |
| 4,820,489 | 4/1989 | Rothe et al. | 422/58 X |
| 4,839,297 | 6/1989 | Freitag et al. | 422/58 X |
| 4,851,210 | 7/1989 | Hewett | 436/531 X |
| 4,861,711 | 8/1989 | Friesen et al. | 436/7 |
| 4,891,313 | 1/1990 | Berger et al. | 435/7.94 |
| 5,037,736 | 6/1991 | Freitag et al. | 436/501 X |
| 5,071,746 | 12/1991 | Wilk et al. | 422/58 X |
| 5,110,550 | 5/1992 | Schlipfenbacher et al. | 422/58 X |

FOREIGN PATENT DOCUMENTS 0194578 9/1986 European Pat. Off. .
0274911 7/1988 European Pat. Off. .
0318777 11/1988 European Pat. Off. .

*Primary Examiner*—Jill A. Johnston
*Assistant Examiner*—Arlen Soderquist
*Attorney, Agent, or Firm*—Nikaido, Marmelstein Murray & Oram

[57] ABSTRACT

Test carrier for the analytical determination of a constituent of a sample fluid by a specific binding reaction between two binding partners having biological affinity. A plurality of test layers is so disposed that they are wetted successively by the fluid and form a fluid transport path, in which one of the test layers is a fixing layer (18) which is a porous carrier matrix. The first of the two binding partners is fixed to the latter. The fluid containing the second binding partner flows through the fixing layer (18), at right angles to its surface, on the test carrier (10).

A largely complete binding reaction in an extraordinarily short time is achieved during the flow through the preferably very thin fixing layer (18) by the fact that a microporous plastics layer with a pore size P of at least 0.01 pm is used as the carrier matrix, and at the same time the size D of the second binding partner and the pore size P of the plastics layer are adjusted to one another so that the pore size P is at least twice and at most ten times as great as the size D of the second binding partner.

38 Claims, 1 Drawing Sheet

TEST CARRIER FOR ANALYTICAL DETERMINATION HAVING A HIGHLY EFFECTIVE FIXING LAYER FOR FLOW-THROUGH BOUND/FREE SEPARATION

The invention relates to a test carrier for the analytical determination of a constituent of a sample fluid by means of a specific binding reaction between two binding partners having biological affinity. The test carrier has a plurality of test layers which are so disposed that they are wetted successively by the fluid and form a fluid transport path.

Qualitative and quantitative analytical determinations are often carried out with the aid of test carriers. Capillary active test layers, which usually consist of absorbent layer materials such as papers, non-woven fabrics or porous plastics materials, are generally fixed in varying arrangements on or to a base element in such a way that the fluid flows through the layers in succession. The test layers contain reagents which are referred to overall as a reagent system and whose reaction with the sample leads to a detection signal in the form of a physically detectable change, and especially a color change, in a detection layer.

Test carriers are known in the form of various external configurations. Of particular practical importance are strip-type test carriers, in which a plastic strip forms the base element on which the test layers are fixed, and also test carriers in the form of square platelets, in which the test layers are enclosed in a frame. In the English literature "test carriers", often are referred to as "solid state analysis elements".

Numerous test carriers have already been proposed for test methods which are based on a specific binding reaction between two binding partners having biological affinity. Specific binding reactions in this context are in particular immunological interactions, i.e. interactions between antigens or haptens, on the one hand, and antibodies, on the other hand. Other specific biological affinity interactions can also be used, however, such as biotin-streptavidine, lectin-sugar or an active substance/ receptor interaction. Reference will be made below, as an example without limitation of the general character, to immunological interactions.

In such tests, the task frequently arises—irrespective of the particular test procedure—of separating the portion bound during a binding reaction from the nonbound portion (bound/free or B/F separation). This separation is carried out in conventional immunological tests by protracted washing and suction steps. In the case of test carrier analysis, a fixing layer is often used for the separation, comprises a porous carrier matrix to which one of the two binding partners in the specific binding reaction is fixed. The fixing layer is so arranged on the test carrier that the fluid containing the second binding partner flows through it. The binding reaction takes place during the flow, i.e. part of the second binding partner is bound to the carrier-fixed first binding partner by virtue of the specific binding reaction and thereby immediately becomes fixed. The non-bound part of the second binding partner remains free to move and flows on through the fixing layer into at least one absorbent layer arranged in the fluid transport path downstream of the fixing layer.

This method of carrying out specific binding reactions including B/F separation on test carriers appears simple. Its realization, however, has proven to be extraordinarily difficult. An initial problem is the long reaction time of specific binding reactions. Although the reaction times of many hours required previously have been substantially reduced by the development of binding partners with particular high reaction rates, the reaction times are still long compared with the time in which the sample fluid is required to pass through a test layer.

Test carriers have therefore been developed for immunological analyses in which the sample fluid passes through the fixing layer, not at right angles to its surface, but parallel to the surface of the fixing layer, i.e. in its longitudinal direction. As with a chromatographic method, a relatively long path (usually in the order of several centimeters) is thereby provided for the course of the binding reaction and the B/F separation. Test carriers of this type are described in U.S. Pat. Nos. 4,361,537 and 4,861,711. Such a design, however, entails high manufacturing costs. The size of the test carriers creates handling difficulties. In addition the long contact time of the sample fluid with the fixing layer can result in a partial reverse reaction taking place, causing a portion of the already bound second binding partner to become detached from the binding sites.

A superior design, therefore, is a test carrier configuration in which the fixing layer is so disposed on the test carrier that the fluid containing the second binding partner flows through the fixing layer at right angles to its surface. Such a test carrier is described for example in EP-A-318 777. Extreme requirements nevertheless have to be met in this design. In particular, the reaction time for the immunological binding reaction is extremely short. It is typically below 10 sec. As complete a binding as possible (more than 90%) nevertheless has to be achieved, in order to achieve sufficient accuracy of the determination. These requirements are increased still further by the fact that modern analytical test carriers operate with extremely small sample amounts (the sample size is typically less than 30 $\mu$l) and the fixing layer is consequently designed extremely thin (typical thickness of less than 0.5 mm).

An object of the present invention is therefore to enable a practically complete binding reaction and separation of the bound portion to take place in an extremely short time, namely during the flow of the fluid sample through the fixing layer at angles to its surface.

This object is achieved with a test carrier of the type described above wherein the carrier matrix of the fixing layer is a microporous plastic layer with a pore size P of at least 0.01 $\mu$m, and the size D of the second binding partner and the pore size P of the plastic layer are adjusted relative to one another so that the pore size P is at least twice and at most ten times as great as the size D of the second binding partner.

The use of porous plastic layers as a carrier matrix for immunological reagent is known. This is mentioned, for example, in DE-A-3 329 728, in which a large number of different materials are compared. EP-A-194 578 and EP-A-274 911 deal specifically with the use of porous plastic membranes as carrier materials for immunological tests. The specific requirements of a thin fixing layer traversed by a flow at right angles to its surface are not however discussed in these documents.

According to the present invention, a substantially complete binding reaction is achieved in an extraordinarily short time during the flow of the sample through an extremely thin microporous plastic fixing layer (thickness preferably less than 0.5 mm, particularly preferably less than 0.25 mm). This result can be attributed to the combination of the measures used:

On the one hand, a minimum value of the plastic layer pore size P has to be met.

On the other hand, at least one of the pore size P and the size D of the second binding partner are adjusted relative to one another in such a way that $P = 2D$ to $10D$.

The second condition is fulfilled, according to a preferred embodiment, by a step wherein the second binding partner is increased in size by chemical bonding to a higher molecular weight, as compared with the molecular weight of its original size.

Surprisingly, this increase leads to a far more rapid and more complete binding, although the total number of binding sites in the second binding partner is not increased.

The increased size of the second binding partner can be achieved by forming an oligomer or polymer of the second binding partner. Aggregates often occur spontaneously during the manufacture of such reagents by conjugation or other reactions. For example, conjugates (AbE) formed from an antibody and an enzyme usually have active groups in the bridge region between the enzyme and the antibody. The practice to date has generally been to select the smallest possible size fractions from the mixture thus obtained, for example with the use of a molecular sieve. The aim of the prior art has generally been to use so-called 1:1 conjugates, in which one antibody is conjugated respectively with one enzyme molecule. In some cases, the enzyme has been reduced further in size by the use of FAB fragments, in order to achieve the highest possible sensitivity.

Other possible methods of increasing the size of the second binding partner are the use of a polymeric labelling enzyme (for example during the manufacture of antibody-enzyme conjugates), or by binding to the second binding partner particles, for example, macromolecules or latex particles, which are inert as regards the biological affinity interaction.

Surprisingly, it has been found in the context of the present invention that the retarded diffusion resulting from the increase in size of the second binding partner does not lead to a rise in the reaction time of the binding reaction.

Numerous microporous plastic layer materials with a highly uniform pore size distribution are commercially available. Their pore size is usually stated by the manufacturer. Polyvinyl difluoride, polyamide, polystyrene and nitrocellulose are particularly suitable plastic layer materials for the invention.

The second binding partner normally occurs as a mixture of different particle sizes. Reference to the particle size D refers to the mean value of the particle sizes of this mixture. The particle size defined in this way can be determined by filtration tests, in which the second binding partner is suspend in a liquid and passed through microporous plastic layers of known pore size and lacking the first binding partner fixed thereto. A particle size D as defined in the present invention is characterised by the fact that at most 10% of the particles are retained by a microporous plastic layer with a pore size P of 1.5 D, while at least 90% of the particles are retained by a microporous plastic layer with a pore size P of 0.67 D.

Oftentimes in practice, an appropriate microporous plastic layer, having a pore size appropriate for the second binding partner, and having a pore size P which is normally greater than 10 times the size D of the second binding partner, will be chosen from a range of commercially available products. The particular plastic material involved is not critical to the present invention, so long as the plastic material does not interfere with the analytical determination, and especially with the specific binding reaction. Once the plastic layer having a given pore size P is selected, then it is a simple matter to adjust the size D of the second binding partner so that the relationship between P and D fits the equation $P = 2D-10D$.

It will be readily apparent to those in the art, however, from the description of the present invention, that it is possible to start from a given second binding partner (which may be a monomer, an oligomer or a polymer) of a given size D, and then select a plastic layer having a suitable pore size P to cause the relation between P and D to fit the above equation. However, as a practical matter, the second binding partner size D will normally be the adjusted variable.

It is of course theoretically possible to adjust both pore size P and second binding partner size D in order to utilize an analytical determination test wherein $P = 2D-10D$. The pore size P could be reduced by coating the pores of the plastic layer with a suitable coating material.

The binding of the first binding partner to the microporous plastic layer can take place by the usual methods known to the art. Reactive organic groups are produced, usually by slight etching, on the surface of the plastic material, to which antigens and antibodies for example can be covalently bound. Such methods are described for example in the references described above, the disclosures of which are hereby incorporated by reference.

BRIEF DESCRIPTION OF THE FIGURES

The invention will be described in greater detail below by means of exemplifying embodiments shown in diagrammatic form in the figures, wherein.

Figure 1:
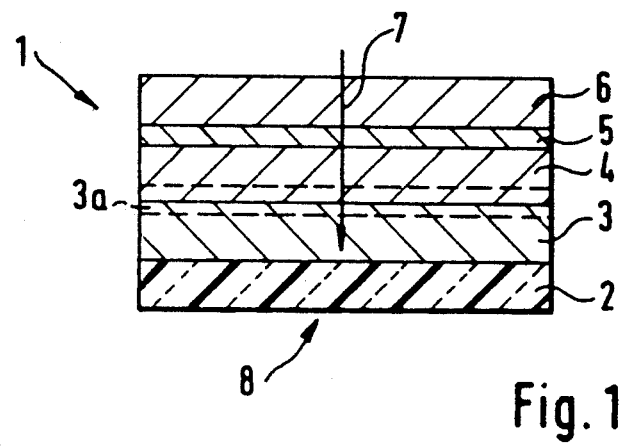
FIG. 1 is a cross-section through the layer sequence of a multilayer test carrier.

The layer sequence, shown in FIG. 1, of a test carrier 1 according to the invention consists of a base layer 2 made of a transparent plastic material, a color detection layer 3, a fixing layer 4, a flow adjusting layer 5 and a conjugate layer 6. The layers 3-6 are fixed onto the base layer 2 in such a way that they are in contact with one another over their whole area, which makes the uniform passage of fluid in a direction at right angles to the layer surface possible. The fluid transport path thereby formed is indicated by the arrow 7.

The function of the test carrier layers shown in FIG. 1 will be explained by means of a test procedure which essentially follows the immune-enzymometric test principle. If, for example, an antigen (Ag) is contained in the sample is to be determined, the analysis takes place as follows.

A drop of sample, for example blood, is introduced onto the conjugate layer 6 and spreads out on layer 6. The layer 6 thus serves as a fluid feed layer for the layers which follow on the fluid transport path 7.

The conjugate layer 6 contains an enzymatically labelled antibody (Ab) for the Ag with the Ab in surplus amount compared with the maximum Ag concentration in the sample. The antibody-enzyme conjugate (AbE) is dissolved by the penetrating fluid sample. At the same time complexes are formed between the AbE and the Ag, which are designated as Ag-AbE. Since a surplus of AbE is present, free AbE remains in the sample after the complex formation.

The flow adjusting layer 5 serves to control the time at which the fluid passes from the conjugate layer 6 into the fixing layer 4. Layer 5 can in particular be designed as a temporary barrier with delayed solubility, and consist of a layer-forming fluid barrier material which is dissolved only slowly by the fluid sample. This method of operation is known to the art and does not need to be described in detail here. The flow control by means of layer 5 makes sure that the complexing between the Ag and the AbE is substantially completed in the conjugate layer 6 before the fluid sample penetrates into the fixing layer 4. It should be emphasized, however, that the flow adjusting layer is optional and can be omitted.

The purpose of the fixing layer 4 is to remove by immunological bonding the non-complexed AbE which would interfer with further performance of the analysis. It contains the Ag binding partner or an analogue of the latter (another substance specifically bindable with the antibody) in carrier-fixed form. During the flow of the fluid through the fixing layer 4, the non-complexed AbE bonds with the carrier-fixed antigen Ag(f), while the Ag-AbE complexes can flow on unimpeded (that is, without being fixed or bonded to the carrier). In this way the desired B/F separation is achieved.

The enzymatically labelled complexes penetrate into the detection layer 3, which contains a color-forming substrate S for the labelling enzyme E. The color of this layer 3 changes due to the reaction between enzyme E and substrate S, and the color formation is indicative of the concentration of the Ag analyzed.

Since the substrate S in the detection layer 3 is usually soluble, there is the risk of substrate S spreading out of the layer 3 into the layer 4 and possibly even into the layers 5 and 6, after it has been dissolved by the sample. In so doing, it would come into contact with labelling enzyme E, and produce color formulation which is not indicative of the analysis. This unwanted color formation can lead to a distortion of the measuring result if color formation is detectable from the evaluation side 8. In order to prevent this distortion, the color detection layer 3 is designed to be optically impermeable, for example by the intercalation of $TiO_2$ particles. It is also possible to provide between the layers 3 and 4 a special optical barrier layer 3a which is permeable to fluid but at least substantially opaque to light. Layer 3a is indicated in dashes in FIG. 1.

The enzymatic immunoassay test principle described is known and therefore does not need to be described in detail. The use of this test principal is preferred for the test carrier according to the invention. An antibody present in the fluid sample can naturally be determined in an analogous manner if antibodies and antigens are respectively exchanged for one another in the layers of the test carrier.

The invention is not, however, limited to such an immunoassay method. On the contrary, the present invention can be used with advantage, irrespective of the details of the analytical determination method used, whenever, during passage through a fixing layer 3 over a very short distance and in a very short time, a practically complete binding reaction has to take place between a carrier-fixed binding partner and a second binding partner transported with the sample fluid.

Figure 2:
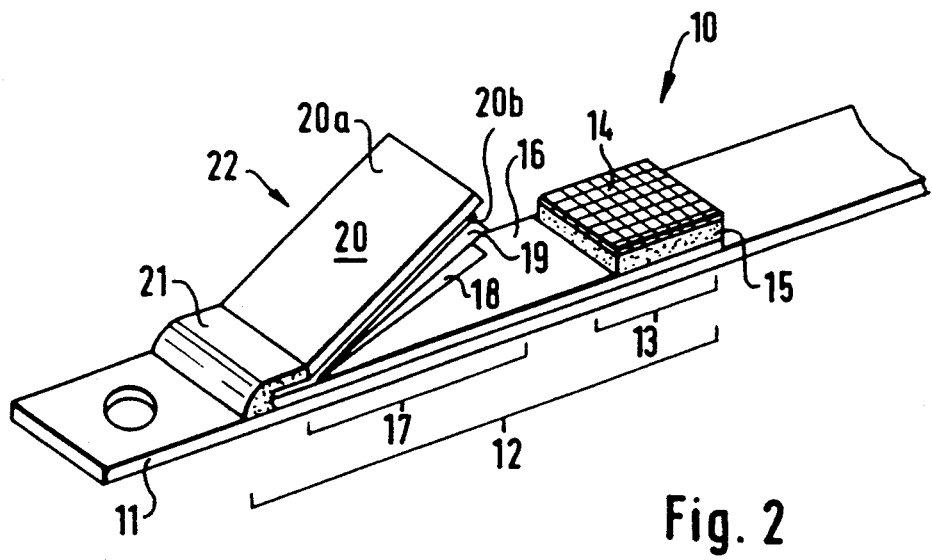
FIG. 2 is a perspective view of an alternative embodiment of a test carrier.

FIG. 2 shows a particularly preferred embodiment, with which an analysis is possible in a short time with high accuracy and using a very small amount of fluid sample.

The test carrier 10 has a detection zone 12 on a base layer 11. The test layers which form the fluid transport path are disposed on detection zone 12.

In a sample introduction zone 13 there is provided under a covering net 14 an erythrocyte separation layer 15. A conjugate layer 16, disposed between the layer 15 and the base layer 11, runs from the sample introduction zone 13 into an evaluation zone 17, and extends parallel to the surface of the base layer 11. In the evaluation zone 17, a fixing layer 18, an optical barrier layer 19 and a color detection layer 20 are fixed in such a way that, with the test carrier 10 in its initial position as shown, these layers do not come into fluid contact with the conjugate layer 16 serving as a fluid feed layer, but the layers 18, 19 and 20 can be brought into fluid communication with the conjugate layer 16 by external manipulation. In the case shown, this arrangement is achieved in a simple manner by the layers 18, 19 and 20 each being fixed at one edge by means of a hot-melt adhesive strip 21 to the base layer 11 in such a way that with the test carrier in its initial position, the layers 18, 19 and 20 stick out obliquely upwards away from the conjugate layer 16 like flaps. This design of a flow control element as a flap, designated overall as 22, is also known and does not need to be explained in detail.

In conjunction with the present invention, the illustrated layer sequence of the separate layers 18, 19 and 20 proves to be particularly advantageous. The fixing layer 18 can according to the present invention be extraordinarily thin, preferably less than 0.5 mm, particularly preferably even less than 0.25 mm, thick. Fixing layer 18 therefore absorbs only a small amount of fluid sample. The color detection layer 20 consists of a backing foil 20a and a reagent film layer 20b, which is coated onto the side of the backing foil 20a facing the conjugate film 16, and layer 20b likewise is designed extraordinarily thin (a layer thickness of less than 200 $\mu$m). This thinness permits an intensive color detection with a small sample amount. A prerequisite for an accurate evaluation of the color formation is an optical barrier layer 19 which is completely impermeable to light. Because of the low fluid sample requirement of the layers 18 and 20b, the optical barrier layer 19 can be designed sufficiently thick (a layer thickness of at least 50 $\mu$m) without the total volume requirement for fluid sample being allowed to rise above the desired upper value (in the exemplifying case 30 $\mu$l). The optical barrier layer can also be coated directly onto the reagent film layer 20b, which results in a further reduction in the fluid absorption.

The test procedure corresponds to that described previously in connection with FIG. 1, with the layer 15 ensuring that the erythrocytes are separated out of the blood so that they cannot disturb the subsequent reaction steps (and in particular the color detection step in the layer 20).

The illustrated flap design of FIG. 2 permits an even more reliable separation in time of the individual reaction steps than in the case of the embodiment according to FIG. 1. This is of particular advantage in conjunction with the excellent B/F separation effect of the fixing layer 18 according to the invention. In the case, for example, of the described reaction sequence prior to the pressing of the flap 18, 19, 20 against the conjugate layer 16, a complete and monitored initial reaction step can first take place, while the subsequent separation reaction by means of the fixing layer 18 takes place rapidly and yet completely. In practice, however, the design with a fixing layer configured in the form of a flap produces an extraordinarily short flow time through the fixing layer 18 (typically less than 10 sec). A sufficient B/F separation effect is nevertheless achieved according to the invention, as is demonstrated below by means of exemplifying embodiments.

EXAMPLE 1

Three models (A, B, and C) of test carriers according to FIG. 2 were manufactured. These models differed from one another only as regards the pore size P of the fixing layer 18 and the particle size D of the conjugate in the conjugate layer 15.

The conjugate layer consists of a glass fibre mat which was coated with polyvinyl alcohol in order to facilitate the dissolution. This layer was impregnated in the case of Model A with a <Theo>-AK-6 galactosidase conjugate (molecular weight M approx. 15 MDa, size D=approx. 0.08 μm) with an activity of 150 mU/cm$^2$. In the case of comparison Models B and C a low-molecular-weight conjugate (M approx. 0.7 MDa, size D=approx. 0.015 μm) of the same conjugate and of the same activity was used.

The fixing layer 18 consisted in the case of models A and B of a microporous plastic material (a polyvinyliden difluoride membrane obtainable e.g. from Millipore, Eschborn, Germany) with a pore size P of 0.2 μm. This carrier matrix was covalently charged with a theophylline-polyhapten (protein coated with theohylline) with a charging density of 50 μg/cm$^2$. In the case of comparison model C, a matrix identical as regards its remaining properties, but with a pore size P of 1.2 μm, was used. The detection layer and the optical barrier layer consisted of a dispersion reagent film with the use of Propriofan (trademark of BASF AG) as film former, in which chlorophenol red galactoside was embedded as a color-forming substrate. The optical barrier layer consisted of titanium dioxide, which was coated directly onto the color detection layer.

By means of the three models, serum or blood containing altogether six different concentrations of theophylline was tested, using the commercially available Reflotron apparatus (trademark of Boehringer Mannheim GmbH). The flap 20 was pressed against the fluid feed layer 16 with a mechanism fitted to this apparatus, the closure time amounting to 0.3 sec. This time was a rough measure of the flow time through the fixing layer 18.

The following time sequence was observed during the course of the reaction:

Prereaction time (dissolution of the conjugate and complexing with the antigen in the sample): 120 sec, followed by closing of the flap;

Measurement of the color formation after 120 sec. The following results are obtained:

| Theophylline mg/L | Model A % rem | Model B % rem | Model C % rem |
| --- | --- | --- | --- |
| 0 | 61.3 | 43.2 | 38.7 |
| 5 | 47.5 | 33.0 | 27.9 |
| 10 | 43.0 | 31.5 | 27.0 |
| 15 | 38.8 | 30.3 | 26.7 |
| 25 | 32.7 | 30.7 | 26.6 |

| Theophylline mg/L | Model A % rem | Model B % rem | Model C % rem |
| --- | --- | --- | --- |
| 39 | 30.1 | 30.5 | 27.6 |

It was found that with Model A according to the invention a total signal range of 30% rem was achieved, whereas far poorer values were observed with the comparison Models (approx. 13% and 11%). The high signal range permits high precision of the analysis for a given accuracy of the optical evaluation. In the case of the comparison tests, the accuracy was far worse. No meaningful evaluation is possible in the range of higher theophylline concentrations.

EXAMPLE 2

Two models (D and E) of test carriers according to FIG. 2 were manufactured, which apart from the following differences were the same as Example 1.

The conjugate layer 15 was impregnated (in addition to, and after, the (Theo)-Ak-6 galactosidase conjugate) with biotinylated theophylline (theo-8-cp-Bi) in a concentration of 0.5 μg/ml. In other respects the layer 15 corresponded in the case of Model D to the layer 15 of Model A (high-molecular-weight conjugate) and in the case of Model E to Models B and C (low-molecular-weight conjugate) of Example 1.

The fixing layer 18 had in the case of both Model D and Model E, a pore size of P=0.65 μm. It was covalently charged with streptavidine with a charging density of approx. 20 μg/cm$^2$.

In the case of both Models, serum with various concentrations of theophylline was measured. The measuring technique was the same as in Example 1, but the flap was closed more slowly. A closing time of 8 sec ensured that the streptavidine was renatured to a sufficient degree after contact with the sample fluid.

The test principle differed in this Example 2 from the test principle described in conjunction with FIG. 2 and Example 1. In the conjugate layer 15 the Ag from the sample forced the biotinylated antigen (B-Ag) out of its bond with the antibody-enzyme conjugate (AbE). B-Ag-AbE and Ag-AbE complexes were formed, with the concentration of the last-named complexes increasing in direct proportion to the amount of antigen which is present in the sample.

After closure of the flap 22 both complexes penetrated into the fixing layer 18, the biotin-containing complexes thereby bonded with the streptavidine and were held fast. In this case also the color formation in the color detection layer 20 was a measure of the antigen concentration.

The following results were obtained for the determination of this Example:

| Theophylline mg/L | Model D % rem | Model E % rem |
| --- | --- | --- |
| 0 | 55.9 | 38.3 |
| 5 | 48.8 | 35.7 |
| 10 | 43.8 | 32.5 |
| 20 | 39.5 | 30.7 |
| 30 | — | 30.4 |
| 40 | 31.7 | — |

It is clear that Model D, which is according to the present invention, produces a larger total signal range than comparative Model E.

We claim:

1. A test carrier for the analytical determination of at least one constituent of a fluid sample using a specific binding reaction between a first binding partner and a second binding partner having biological affinity for each other, said test carrier comprising a plurality of test layers forming a fluid transport path and disposed so that the plurality of test layers are wetted successively by fluid flowing along said fluid transport path, said plurality of test layers including a fluid feed layer, a fixing layer and an absorbent layer, aid fluid feed layer being provided in said fluid transport path upstream in the direction of fluid flow from said fixing layer and said fluid feed layer having said second binding partner contained therein so that as fluid flows through said fluid feed layer, said second binding partner is dissolved in said fluid, said fixing layer comprising a porous carrier matrix to which said first binding partner is fixed, said porous carrier matrix comprising a microporous plastic layer having a pore size P of at least 0.01 μm, said fixing layer having a major surface and being disposed in relation to the rest of the test carrier such that fluid sample containing said second binding partner dissolved therein flows through said fixing layer at right angles to said major surface, said second binding partner having a size D which is in relation to the plastic layer pore size P such that P is at least twice and at most ten times as great as D, said absorbent layer being provided in the fluid transport path downstream in the direction of fluid flow from said fixing layer and including detection means for detecting said second binding partner.

2. The test carrier of claim 1, wherein to provide the P to D size relation said second binding partner is bound to at least one additional molecular without destroying the biological affinity of said second binding partner for said first binding partner.

3. The test carrier of claim 2, wherein the higher molecular weight form of the second binding partner is an oligomer or polymer of a monomeric form of the second binding partner.

4. The test carrier of claim 2, wherein the second binding partner is chemically bonded to a third binding partner which is inert as to the biological affinity binding reaction of the first and second binding partners.

5. The test carrier of claim 1, wherein the first binding partner comprises streptavidine and the second binding partner comprises biotin.

6. The test carrier of claim 1, wherein an opaque, optical barrier layer is disposed between said fixing layer and said absorbent layer.

7. The test carrier of claim 1, wherein the thickness of the fixing layer is less than 0.5 mm.

8. The test carrier of claim 7, wherein said thickness is less than 0.25 mm.

9. The test carrier of claim 1, further including a flow adjusting means disposed in the fluid transport path for regulating the time at which the fluid sample flows through said fixing layer.

10. The test carrier of claim 9, wherein said fixing layer, and said absorbent layer are located in the form of a flap out of fluid contact with, said fluid feed layer when the test carrier is in a pre-test state.

11. The test carrier of claim 1, wherein said plastic layer comprises a polymer selected from the group consisting of a vinyl polymer, a polyamide, a polystyrene or nitrocellulose.

12. The test carrier of claim 1, wherein said plastic layer comprises polyvinyl difluoride.

13. A method for conducting an analytical determination of at least one constituent of a fluid sample by means of a specific binding reaction between a first binding partner and a second binding partner having biological affinity for each other, said method comprising passing the fluid sample through the test carrier of claim 1.

14. A test carrier for use in the analytical determination of a constituent of a fluid sample using a specific binding reaction between two binding partners having mutual biological affinity, and comprising a first binding partner nd a second binding partner, said test carrier comprising a plurality of test layers disposed to be wetted successively by the fluid ample and forming a fluid transport path, said plurality of test layers including fluid feed layer means, fixing layer means and absorbent layer means, said fluid feed layer means being provided in said fluid transport path upstream in the direction of fluid flow from said fixing layer means and said fluid feed layer means having said second binding partner contained therein so that as fluid flows through said fluid feed layer means, said second binding partner is dissolved in said fluid, said fixing layer means for having a binding reaction with said second binding partner in the fluid sample flowing through the fixing layer means to bind said second binding partner to said fixing layer means, said fixing layer means being generally planar having a major plane surface and comprising a porous carrier matrix having said first binding partner fixed thereto, said fixing layer means being disposed in relation to the rest of the test carrier such that said fluid sample containing said second binding partner flows through said fixing layer means at right angles to said major plane surface thereof, said porous carrier matrix comprising a microporous plastic layer having a pore size P of at least 0.01 μm, the size D of said second binding partner and said plastic layer pore size P being in relation to each other such that P=2D to 10D, said absorbent layer means for absorbing fluid passing through and downstream of the fixing layer means, and said absorbent layer means including detection means for detecting said second binding partner.

15. A test carrier for the analytical determination of at least one constituent of a fluid sample using a specific binding reaction between a first binding partner and a second binding partner, said second binding partner being capable of binding with said at least one constituent of said fluid sample to form a complex, said first binding partner and said second binding partner having biological affinity for each other, and said first binding partner and said complex not having a biological affinity with each other, said test carrier comprising a plurality of test layers forming a fluid transport path and disposed so that said plurality of test layers are wetted successively by fluid flowing along said fluid transport path, said plurality of test layers including a fluid feed layer, a fixing layer and an absorbent layer, said fluid feed layer being provided in said fluid transport path upstream in the direction of fluid flow from said fixing layer and said fluid feed layer having said second binding partner contained therein so that as fluid flows through said fluid feed layer, said second binding partner is dissolved in said fluid, said fixing layer comprising a porous carrier matrix to which said first binding partner is fixed, said porous carrier matrix comprising a microporous plastic layer having a pore size P of at least 0.01 µm, said fixing layer have a major surface and being disposed such that fluid sample containing said second binding partner nd said complex, if present, flows through said fixing layer at right angles to said major surface, said second binding partner having a size D which is in relation to said plastic layer pore size P such that P is at lest twice and at most ten times as great as D, said absorbent layer being provided in said fluid transport path downstream in the direction of fluid flow from said fixing layer, and said absorbent layer including means to detect the presence of said complex.

16. The test carrier of claim 15, wherein to provide the P to D size relation of said second binding partner is bound to at least one additional molecule without destroying the biological affinity of said second binding partner for said first binding partner.

17. The test carrier of claim 15, wherein said higher molecular weight form of said second binding partner is an oligomer or polymer of a monomeric form of said second binding partner.

18. The test carrier of claim 16, wherein said second binding partner is chemically bonded to a third binding partner which is inert as to the biological affinity binding reaction of said first and second binding partners.

19. The test carrier of claim 15, wherein said first binding partner comprises streptavidine and said second binding partner comprises biotin.

20. The test carrier of claim 15, wherein an opaque, optical barrier layer is disposed between said fixing layer and said absorbent layer.

21. The test carrier of claim 15, wherein the thickness of said fixing layer is less than 0.5 mm.

22. The test carrier of claim 21, wherein said thickness is less than 0.25 mm.

23. The test carrier of claim 14, further including a flow adjusting means disposed in said fluid transport path for regulating the time at which the fluid sample flows through said fixing layer.

24. The test carrier of claim 15, wherein said plastic layer comprises a polymer selected form the group consisting of a vinyl polymer, a polyamide, a polystyrene or nitrocellulose.

25. The test carrier of claim 15, wherein said plastic layer comprises polyvinyl difluoride.

26. A method for conducting an analytical determination of at least one constituent of a fluid sample by means of a specific binding reaction between a first binding partner and a second binding partner having biological affinity for each other, said method comprising passing the fluid sample through the test carrier of claim 15.

27. A test system for the analytical determination of at least one constituent of a fluid sample, said test system comprising a test carrier, a first binding partner and a second binding partner, said second binding partner being capable of binding with said at least one constituent of said fluid sample to form a complex, said first binding partner and said second binding partner having biological affinity for each other, and said first binding partner and said complex not having a biological affinity with each other, said test carrier comprising a plurality of test layers including a fixing layer and an adsorbent layer and having a first and second state wherein the test carrier can be placed in the second state from the first state, and wherein when the test carrier is in said second state, said plurality of test layers form a continuous fluid transport path and are disposed so that said plurality of test layers are wetted successively by fluid flowing along said fluid transport path, and when said test carrier is in said first state, said plurality of test layers do not form a continuous fluid transport path, said fixing layer comprising a porous carrie matrix to which said first binding partner is fixed, said porous carrier matrix comprising a microporous plastic layer having a pore size P of at least 0.1 µm, said fixing layer having a major surface and being disposed in relation to the rest of the test carrier such that when the test carrier is in said second state, fluid sample containing said second binding partner and said complex, if present, flows through said fixing layer at right angles to said major surface, said second binding partner having a size D, which is in relation to the plastic layer pore size P such that P is at least twice and at most ten times as great as D, said absorbent layer being provided in said fluid transport path downstream in the direction of fluid flow from said fixing layer, and said absorbent layer including means to detect the presence of said complex.

28. A test carrier for the analytical determination of at least one constituent of a fluid sample using a specific binding reaction between a first binding partner and a second binding partner having biological affinity for each other, said test carrier comprising a plurality of test layers including a fluid feed layer, a fixing layer and an absorbent layer and having a first and second state wherein the test carrier can be placed in the second state from the first state, wherein when the test carrier is in said second state, said plurality of test layers form a continuous fluid transport path and are disposed so that said plurality of test layers are wetted successively by fluid flowing along said fluid transport path, and when said test carrier is in said first state, said plurality of test layers do not form a continuous fluid transport path, said fluid feed layer being provided in said fluid transport path upstream in the direction of fluid flow from the fixing layer and said fluid feed layer having said second binding partner contained therein so that as fluid flows through said fluid feed layer, said second binding partner is dissolved in said fluid, said fixing layer comprising a porous carrier matrix to which the first binding partner is fixed, said porous carrier matrix comprising a microporous plastic layer having a pore size P of at least 0.01 µm, said fixing layer having a major surface and being disposed in relation to the rest of the test carrier such that when the test carrier is in said second state, fluid sample containing said second binding partner flows through said fixing layer at right angles to said major surface, said second binding partner having a size D which is in relation to the plastic layer pore size P such that P is at least twice and at most ten times as great as D, said absorbent layer being provide din the fluid transport path downstream in the direction of fluid flow from said fixing layer, and said absorbent layer including detection means for detecting said second binding partner.

29. The test carrier of claim 28, wherein to provide the P to D size relation of said second binding partner is bound to at least one additional molecular without destroying the biological affinity of said second binding partner for said first binding partner.

30. The test carrier of claim 29, wherein said higher molecular weight form of said second binding partner is an oligomer or polymer of a monomeric form of said second binding partner.

31. The test carrier of claim 29, wherein said second binding partner is chemically bonded to a third binding partner which is inert as to the biological affinity binding reaction of said first and second binding partners.

32. The test carrier of claim 28, wherein said first binding partner comprises streptavidine and said second binding partner comprises biotin.

33. The test carrier of claim 28, wherein an opaque, optical barrier layer is disposed between said fixing layer and said absorbent layer.

34. The test carrier of claim 28, wherein the thickness of said fixing layer is less than 0.5 mm.

35. The test carrier of claim 28, wherein said thickness is less than 0.25 mm.

36. The test carrier of claim 28, wherein said fixing layer is in fluid contact with said fluid feed layer only when the test carrier is in the second state.

37. The test carrier of claim 33, wherein said fixing layer, said opaque, optical barrier layer and said absorbent layer are located in the form of a flap above, and out of fluid contact with, said fluid feed layer when the test carrier is in said first state.

38. A method for conducting an analytical determination of at least one constituent of a fluid sample by means of a specific binding reaction between a first binding partner and a second binding partner having biological affinity for each other, said method comprising passing the fluid sample through the test carrier of claim 28.

* * * * *